United States Patent [19]

Strawn

[11] Plant 4,636

[45] Feb. 3, 1981

[54] MINIATURE ROSE PLANT

[76] Inventor: Leslie E. Strawn, 10422 Morningside Ave., Garden Grove, Calif. 92643

[21] Appl. No.: 94,817

[22] Filed: Nov. 15, 1979

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by creamy white and coral pink buds and flowers of distinctive form and further indentified by the erect, dwarf, compact plant.

1 Drawing Figure

1

The present invention relates to a new and distinct variety of hardy, dwarf, bush type rose plant of the miniature class; the variety being primarily characterized — as to novelty — by the creamy white and coral pink buds and flowers which in general effect are similar to Magic Carrousel (U.S. Plant Pat. No. 3,601).

The variety is further characterized by:

An abundance of bloom, with flowers borne one to a stem. No side buds.

Light sweet fragrance.

A plant which is vigorous, of upright growth habit with semi-glossy foliage with pointed leaflets; the buds and flowers being similar in form and size to the pollen parent, Sheri Anne (Miniature — U.S. Plant Pat. No. 3,826).

The plant, which has a normal height of 12 to 14 inches, can easily be maintained at lesser height by occasional trimming.

A plant which grows and blooms satisfactorily both in a greenhouse or outdoors; is good for growing in pots; and provides excellent garden decoration as well as cut flowers.

The present variety of miniature rose was originated by me in my home greenhouse, located at Garden Grove, Orange County, Calif., under conditions of careful control and observation, as a cross between Neue Revue (Hybrid Tea, non patented) as the seed parent and Sheri Anne (Miniature — U.S. Plant Pat. No. 3,826) as the pollen parent.

Subsequent to origination of the variety I successfully asexually reproduced it in my garden, located as foresaid, (also propagated by Pixie Treasures Rose Nursery, 4121 Prospect Ave., Yorba Linda, Orange County, Calif., by budding as well as by cuttings; the reproductions havng run true in all respects.

The color photograph illustrates the variety, including the foliage, buds and flowers.

Referring now specifically to the new and distinct variety of miniature, rose plant, the following is a detailed description thereof in outline; all major color plate identifications being by reference to the British Colour Council Horticultural Colour Chart, except where common terms of color definition are employed.

Type: Hardy: dwarf; bushy; upright; seedling; greenhouse; outdoors; cut flowers; garden decoration; potted plant.

Class: Miniature.

*Variety name.*—Pink Petticoat.

Flowers borne: Singly on upright, slender stems.

2

Quantity of bloom: Abundant both outdoors and in greenhouse.

Bud:

*Peduncle.*—Medium length; slender but sturdy; erect; medium green, sometimes tinted bronze (outdoors); Hairs — none;Bristles — very, very tiny.

*Before calyx breaks.*—Size — small. Form — pointed; medium long; with foliaceous parts extending beyond the tip of the bud equal to one-half of its length. Color — medium green.

*As calyx breaks.*—Color — near Vermilion 18/1 on one third of petal with base near white. Opening — opens well in all weather.

Bloom:

*Size when fully open.*—Small, averaging about 4 cm (1½ in.).

*Petalage.*—Double — averaging about 30 to 35 petals, arranged regularly plus a few small petaloids.

*Form.*—Full at first becoming rounded with medium high center, with petals rolled loosely outward; and later at maturity, full with petals rolled at edge to give a pointed effect and arranged loosely outward and upward. Open flowers show stamens.

Petals: Medium thickness; satiny on inside and outside surfaces.

*Shape.*—Outside petals, broad lanceolate with acute tip and wedge shaped base; intermediate petals — medium broad lanceolate with acute tip; inside petals — narrow lanceolate with acute tip.

Color: One half to three quarters open flower from a plant grown outdoors at Pixie Treasures Rose Nursery, Yorba Linda, Calif., October 1979.

*Outside petal.*—Outside surface — near Azalea Pink 618 on the outer third of area with a fine pencil line of a slightly deeper shade on the very edge; center area — creamy white; very light greenish white at base. Inside surface — near Coral Pink 0619 on the outer third of area; center area creamy white; very light yellow green at base.

*Intermediate petal.*—Outside surface — near Azalea Pink 618 on the outer quarter of area with a fine pencil line of a slightly deeper shade on the very edge; center area light creamy white; very light greenish white at base. Inside surface — near Coral Pink 0619 on the outer quarter area;

center area light creamy white; very light greenish white at base.

*Inner petal.*—Outside surface — same as intermediate petal; inside surface — same as intermediate petal.

General color effect: Newly opened flowers — symmetrical arrangement of creamy white petals bordered with a lively coral pink.

*Three days open.*—Color similar to newly open flowers; open center; stamens showing.

*Six to seven days.*—Old petals drop off (separate at top of calyx tube).

*Behavior.*—Opens well in all weather. Flower longevity (Oct. 1979) — plant in ground — 5-6 days; plant in pot — 4-5 days or longer; cut flowers at living room temperature — 3-4 days or longer; Hardy, disease resistant. Relatively fast grower.

Reproductive organs:

*Stamens.*—50 to 60.

*Filaments.*—3 to 5 mm length, pale yellow green.

*Anthers.*—1 to 2 mm, golden yellow, introse.

*Pollen.*—Moderate amount.

*Pistils.*—Project above disc.

*Styles.*—Several, 5 mm length, bunched, color reddish.

*Ovaries.*—All enclosed in calyx.

*Hips.*—Globular, form readily.

*Sepals.*—Permanent, spear shaped, reflexed.

*Seed.*—Develop readily, moderate number.

Foliage:

*Leaves.*—Compound of five or seven leaflets, usually five; small — varying 4 cm to 7 cm length; leathery; semi-glossy.

*Leaflets.*—Shape ovate; acute apex; base rounded; almost no petiolule; margin serrate.

*Rachis.*—Medium strength; upper side grooved; underside may have a few soft thorns.

*Stipules.*—Very pointed auricles; smooth side edges.

*Color.*—Medium green; new growth — may have reddish veins and margin.

Growth:

*Habit.*—Dwarf; bushy; erect; much branched.

*Growth.*—Vigorous; internodes short.

*Canes.*—Medium; slender; sturdy.

*Main stems.*—Color — medium green.

*Thorns.*—Needle shape; declining; very few; color — light tan; prickles — none; hairs — none.

*Branches.*—Color — medium to light green; thorns — very few; medium base; prickles — none; hairs — none.

*Young shoots.*—Reddish green; thorns—very few; tiny, slender, very straight and reddish.

The miniature rose plant and its flowers as herein described may vary in slight detail due to climatic, soil and cultural conditions under which the variety may be grown.

The following is claimed:

1. A new and distinct variety of miniature rose plant of hardy, dwarf, bushy, erect, much branched habit, substantially as illustrated and described, characterized by buds and flowers of creamy white with petals bordered in a coral pink, the buds and flowers resembling Magic Carrousel (U.S. Plant Pat. No. 3,601) in color pattern and Sheri Anne (U.S. Plant Pat. No. 3,826) in vigor, form and size, having buds and flowers of a distinctive and unique appearance as compared to other miniature roses, flowers being in a new color combination, being vigorous and compact with abundant foliage, ease of propagation from soft wood cuttings or by budding, and with an abundance of flowers.

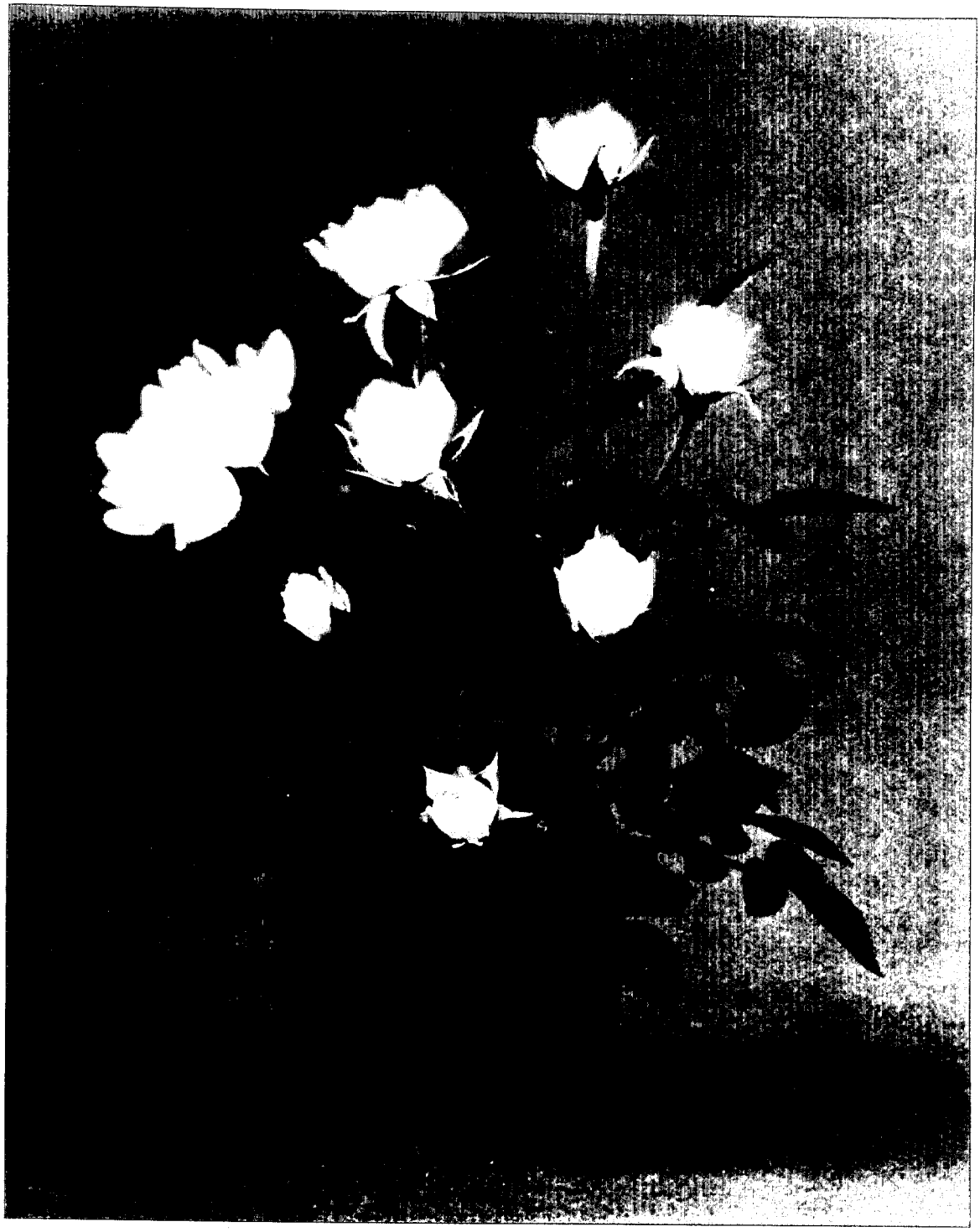

* * * * *